United States Patent [19]

Schepky et al.

[11] Patent Number: 4,863,724
[45] Date of Patent: Sep. 5, 1989

[54] ANTI-DIABETIC PHARMACEUTICAL COMPOSITIONS AND THE PREPARATION THEREOF

[75] Inventors: Gottfried Schepky, Biberach; Rolf Brickl, Warthausen; Eckhard Rupprecht, Aulendorf-Tannhausen; Andreas Greischel, Biberach, all of Fed. Rep. of Germany

[73] Assignee: Dr. Karl Thomae GmbH, Bieberach an der Riss, Fed. Rep. of Germany

[21] Appl. No.: 76,697

[22] Filed: Jul. 23, 1987

[30] Foreign Application Priority Data

Jun. 8, 1983 [DE] Fed. Rep. of Germany ....... 3320582

[51] Int. Cl.⁴ ............................................. A61K 31/79
[52] U.S. Cl. .................................. 424/80; 514/866
[58] Field of Search ....................... 424/80; 514/866; 562/493

[56] References Cited

U.S. PATENT DOCUMENTS 3,708,481  1/1973  Kufter ............................. 514/866
4,696,815  9/1987  Schepky ............................ 424/80

Primary Examiner—William R. Dixon, Jr.
Assistant Examiner—James M. Hunter, Jr.
Attorney, Agent, or Firm—Felfe & Lynch

[57] ABSTRACT

Galenic compositions containing an oral antidiabetic agent and having an improved release of active substance are provided, as well as processes for producing these compositions. The compositions are characterized in that the onset of the activity and the duration of activity are adapted to the particular needs of diabetics with regard to proper control of the metabolism and the associated proper release of insulin. A basic or acidic excipient in a solvent is added to the antidiabetic active substance in a quantity such that the active substance is made soluble, and then a solubilizing agent is added. Polyvinylpyrrolidone is dissolved as carrier in this solution, but the carrier may simultaneously serve as the solubilizing adjuvant. This solution is further processed with other excipients to form pharmaceutical compositions.

17 Claims, 5 Drawing Sheets

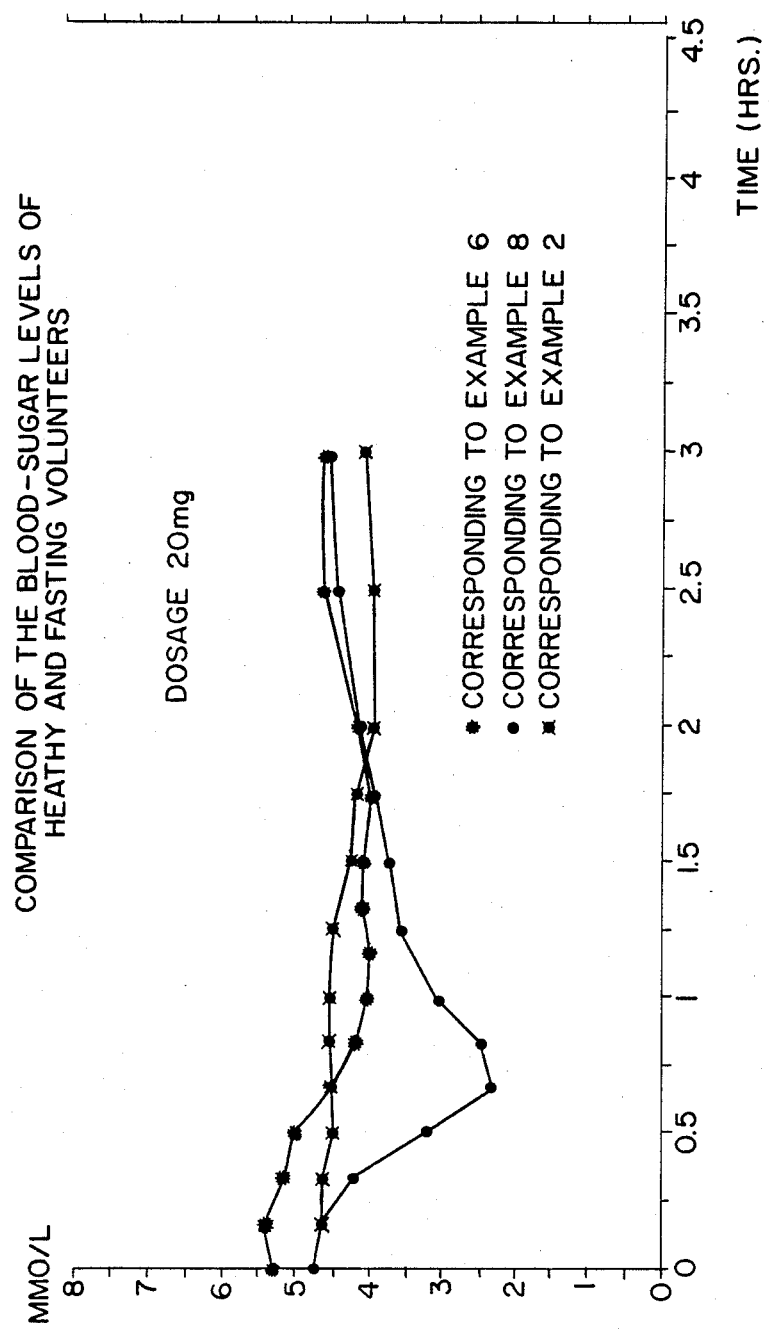

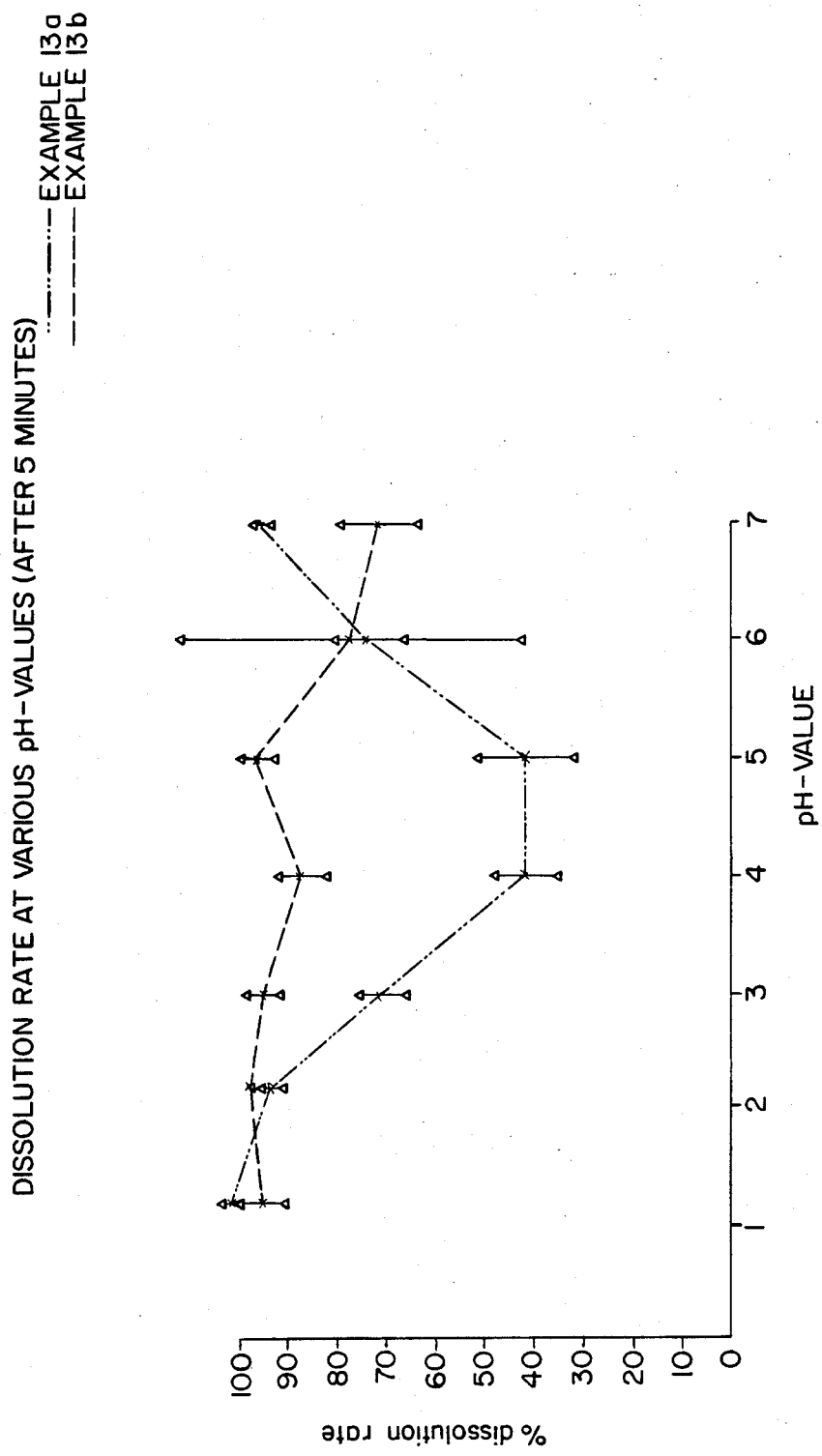

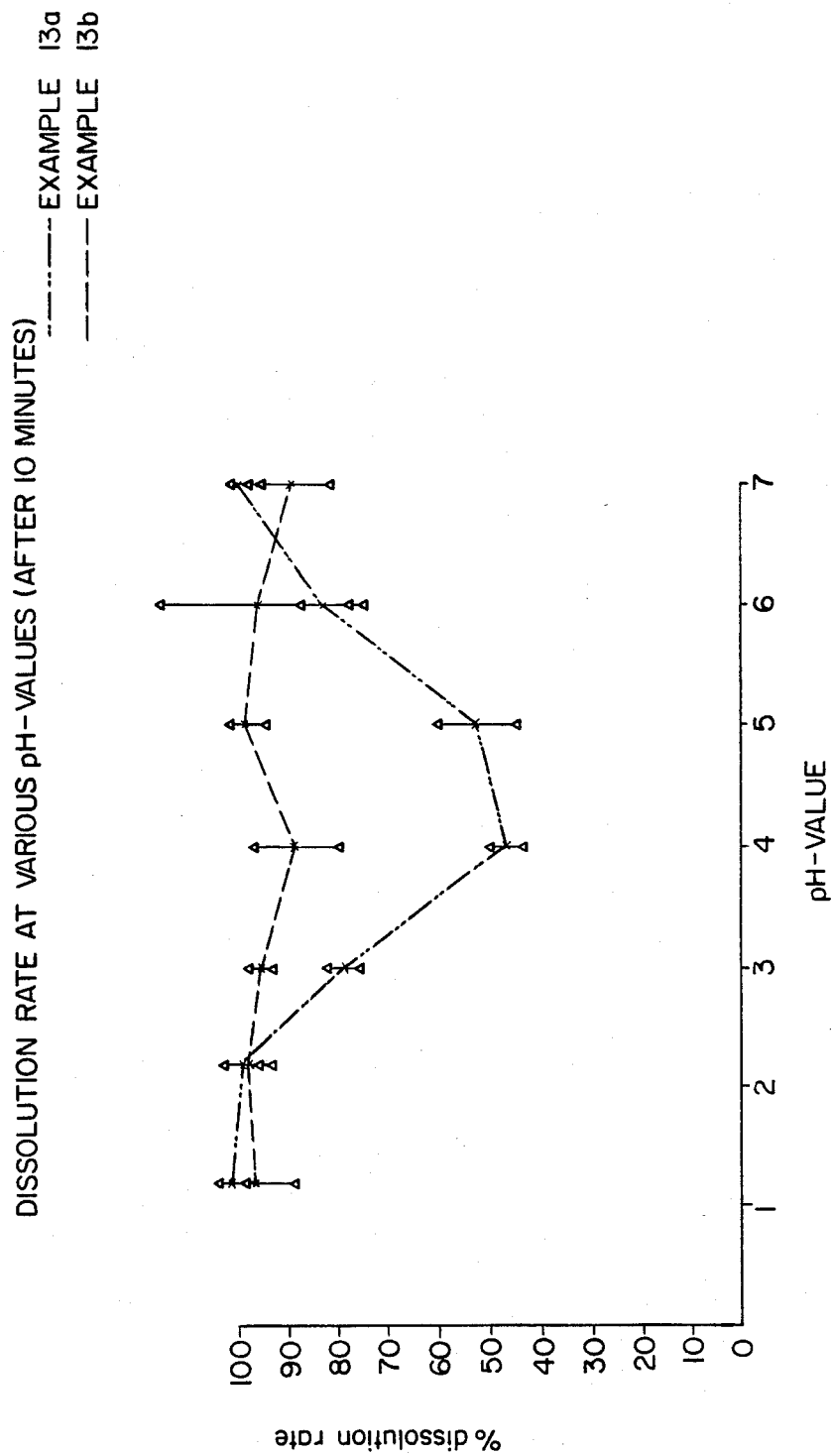

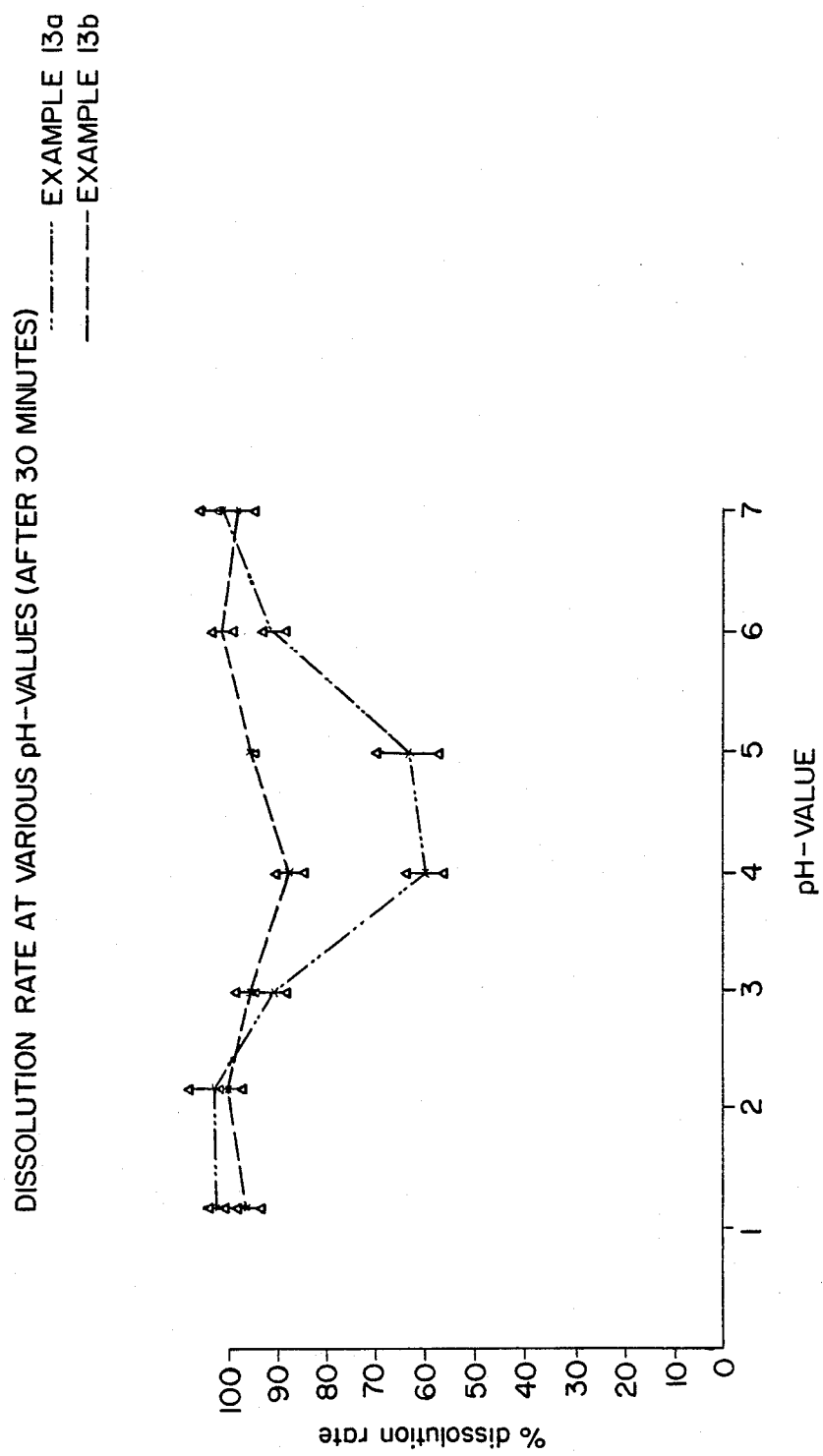

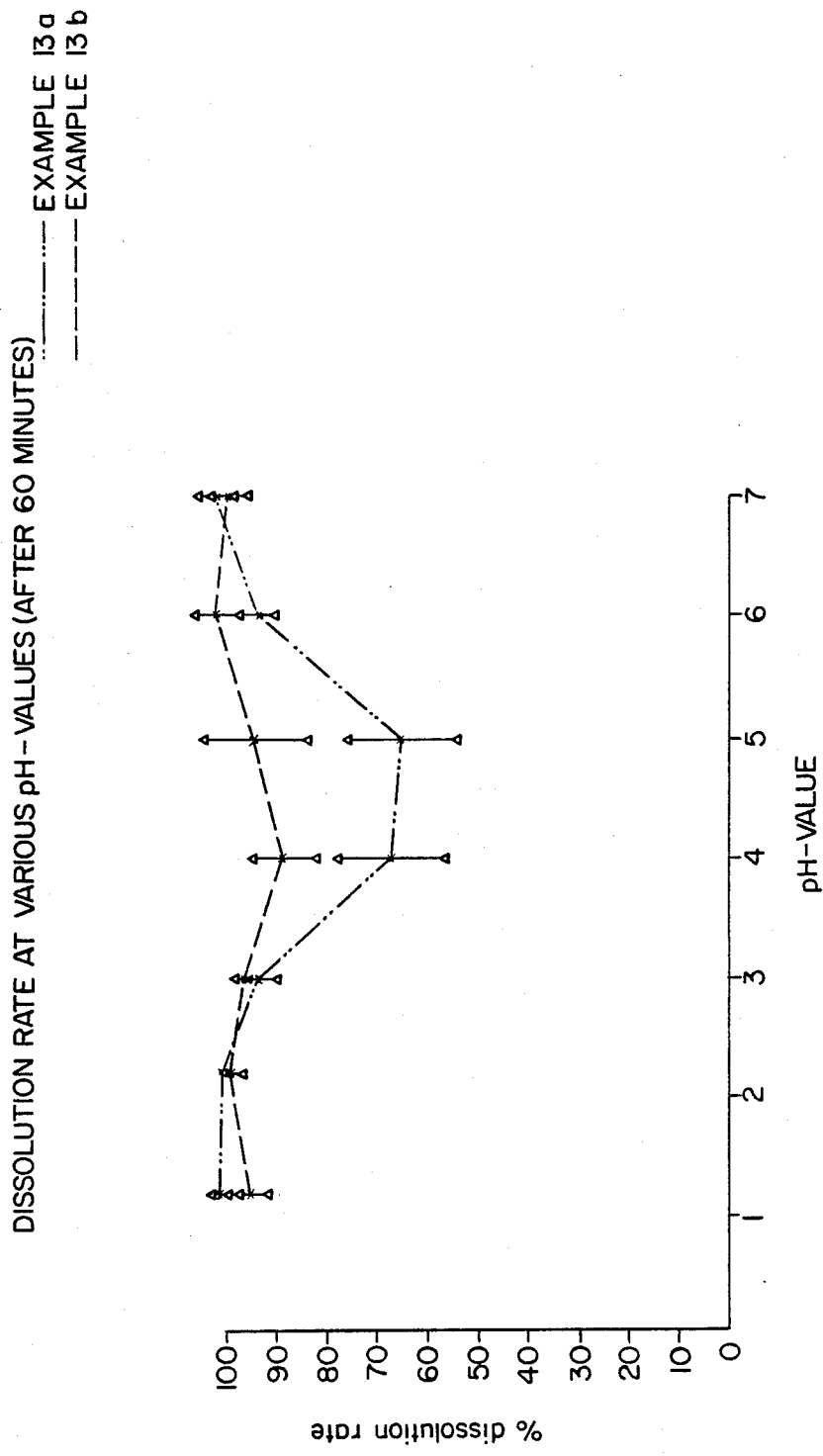

ANTI-DIABETIC PHARMACEUTICAL COMPOSITIONS AND THE PREPARATION THEREOF

This is a continuation-in-part of copending application Ser. No. 615,892, filed May 31, 1984 now U.S. Pat. No. 4,696,815, issued Sept. 29, 1987.

FIELD OF INVENTION

This invention relates to novel pharmaceutical compositions, and, more particularly, to oral anti-diabetic pharmaceutical compositions and the preparation thereof.

BACKGROUND OF THE INVENTION

Generally, in connection with the oral administration of substances which are difficultly soluble in the digestive fluids, such as the anti-diabetic substances mentioned below, the following problems arise: in many cases the active substance can only be partly absorbed, and greatly fluctuating blood levels of the active substance may occur inter- and intra-individually. However, in oral anti-diabetic agents, the start of the activity and the duration of the activity are also of particular importance since the activity should be matched to the blood sugar levels caused by the intake of food. This is not the case with the previously available preparations of anti-diabetic agents in which the effect of the substance and physiological insulin requirements in accordance with the intake of food cannot be reliably matched to one another in terms of time. The activity of the substance often occurs too late: -frequently the maximum effect is only achieved at a time at which the blood glucose values are already dropping, even without medication, after the intake of food. Then, the activity of the substance continues even when the blood glucose has returned to its initial level (see Berger, in Pelzer and Froesch, Diabetische Enteropathie, Hypoglykämien, Verlag Hans Hüber, Bern-Stuttgart-Wien 1974).

Attempts have been made to synchronize the hypoglycemic activity of a sulfonyl urea with the increase in blood sugar caused by food intake by taking the sulfonyl urea at a suitable time before the meal. However, it was then found that administration of the active substance thirty minutes before the meal did not result in a satisfactory improvement in activity [see Sartor et al., Eur. J. Clin. Pharmacolog. 21, 403 to 408 (1982)], partly because of the longer duration of activity mentioned above. Furthermore, a specific time difference between the taking of the medicine and the taking of food can only be reliably monitored in a clinic.

Attempts have also been made to solve these problems in the case of substances which are difficultly soluble in the digestive fluids by attempting to optimize the dissolution rate of the active substance, difficultly soluble per se, in the development of the galenic preparations. This was done, for example, by increasing the surface area of the active substance. Thus, German Patent No. 2,348,334 discloses a preparation form in which the active substance (also a hypoglycemic substance) is present with a particle surface area of from 3 to 10 $m^2/gm$ in the presence of a wetting agent. However, this objective was also supposed to be achieved by applying the active substance in dissolved form to a substrate or carrier with the largest possible surface area and then removing the solvent [cf. H. Rupprecht, Acta Pharm. Technol. 26/1, pages 13 ff. (1980)].

Furthermore, attempts have been made to improve the dissolution rate by adding salt-forming agents (see German Offenlegungsschrift No. 31 24 09). However, to improve the solubility and the dissolution rate, solid dispersions were also produced. They consisted of the active substance and one or more water-soluble carriers, possibly combined with surface-active substances. To prepare these dispersions, a homogeneous melt is prepared from the active substance or possibly a salt thereof and a carrier (see German Offenlegungsschrift No. 23 55 743). In another process, the active substance and carrier are dissolved in a common solvent, and then the solvent is eliminated. The water soluble carriers used are, inter alia, polyvinylpyrrolidone or polyethylene glycols [see H. R. Merkle, Acta Pharm. Technol. 27/4, pages 193 ff. (1981); and W. L. Chiou, S. Riegelmann, J. Pharm. Sci. 60/9, 1281 ff. (1971)].

If the methods in the literature described below are used to produce preparations containing anti-diabetic substances, a better dissolution rate for the active substance, such as gliquidone, is scarcely obtained: the salt formation itself does not result in an increase in the dissolution rate (see Table 4, Example 6), and the application of active substance, such as gliquidone, to a carrier alone (see page 9, line 24 to page 10, line 10 below) does not produce the desired result either. In corresponding tests, which will be described in more detail hereinafter, the dissolution rate was determined, and in the case of gliquidone it was found to be no greater than the dissolution rates shown by known gliquidone-containing preparations.

OBJECTS OF THE INVENTION

It is an object of the invention to provide novel pharmaceutical forms.

It is also an object of the invention to provide oral anti-diabetic pharmaceutical forms.

It is a further object of the invention to provide a process for preparing said oral anti-diabetic preparations.

These and other objects of the invention will become more apparent in the discussion below.

DETAILED DESCRIPTION OF THE INVENTION

We have discovered that preparation forms containing compounds with a very rapid and total release of the active substance, can be produced by dissolving (a) acidic active substances by means of basic excipients, (b) amphoteric active substances by means of basic or acidic excipients, or (c) basic active substances by means of acidic excipients in a solvent in the presence of one or more solubilizing substances comprising polyvinylpyrrolidone and, optionally, other solubilizing substances. The solution is evaporated to dryness and optionally processed further to form the desired pharmaceutical composition. The invention also relates to the compositions thus obtained. In any case, however, the molar ratio of active substance to basic or acidic excipient must be selected so that there is an excess of basic or acidic excipient.

It is important that sufficient basic or acidic excipient is added to the active substance to ensure rapid and complete dissolution in vivo. This is only possible with a molar ratio of substance to basic or acidic excipient of less than 1:1.

The oral anti-diabetic compositions contain as active substances anti-diabetic sulfonyl ureas, such as gliquidone, or anti-diabetic benzoic acids. Other anti-diabetic sulfonyl ureas include glibenclamide, glibornuride, glisoxepide, glipizide and gliclazide. Gliquidone is 1-cyclohexyl-3-[[p-[2-(3,4-dihydro-7-methoxy-4,4-dimethyl-1,3-dioxo-2-(1H)-isoquinolyl)ethyl]phenyl]-sulfonyl]urea, which has an hypoglycemic effect. Anti-diabetic benzoic acids include, but are not limited to, 4-[2-(aroylamino)-ethyl]-benzoic acids of the formula

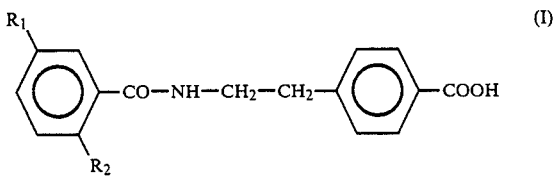

wherein $R_1$ is halogen, preferably chlorine, and $R_2$ is alkoxy of 1 to 3 carbon atoms, preferably methoxy, piperidin-1-yl or octamethyleneimino, and substituted 4-(aralkylaminocarbonylmethyl)-benzoic acids of the formula

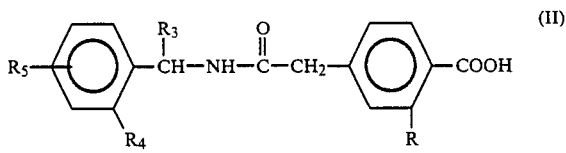

wherein R is hydrogen or ethoxy, $R_3$ is alkyl of 1 to 4 carbon atoms, preferably n-propyl, or phenyl, $R_4$ is piperidino, pyrrolidino, or hexamethyleneimino, and $R_5$ is hydrogen, halogen, preferably chlorine or fluorine, methyl or methoxy.

Mixtures of these active substances may also be used.

The solutions are prepared with polyvinylpyrrolidone as a solubilizing agent. After evaporation, this substance also acts as a carrier at the same time. It is not possible to incorporate the active substance and basic excipient directly in a melt of polyvinylpyrrolidone since this carrier decomposes even before reaching the melting point.

Suitable basic excipients include a number of inorganic or organic bases which are physiologically harmless, that is, pharmaceutically acceptable, at least in the dosage ranges used, such as sodium hydroxide, potassium hydroxide, ammonia, tert.-sodium phosphate, diethanolamine, ethylenediamine, N-methylglucamine or L-lysine. The molar ratio of active substance to basic excipient or mixtures of excipients is preferably from about 1:1.1 to 1:10, but a greater excess of base may also be advantageous in some cases.

Suitable acidic excipients include sulfuric and phosphoric acid and organic acids such as tartaric acid. The acid must be present in excess.

To stabilize highly concentrated solutions such as those which are clearly obtained when using a preparation according to the invention, it is necessary to add polyvinylpyrrolidone as a solubilizing and/or emulsifying substance. Additionally, other such substances can be included such as polyoxyethylene polyoxypropylene polymers, polyethylene glycol 4000 or 6000, polyethoxylated sorbitan mono-oleates, sobitol, glycerol polyethylene glycoloxy stearates, and polyoxyethylene fatty alcohol ethers. Both the nature of the solubilizing substance and also the proportions used are important in determining the dissolution rate of the active substance. The ratio of active substance, to the total quantity of solubilizing substances is from about 1:0.5 to 1:10 by weight.

The solution of the active substance, basic or acidic excipients, and solubilizing and/or emulsifying substances is prepared primarily using water or other polar solvents, for instance lower alcohols, such as ethanol or isopropanol, ketones such as acetone, or mixtures of these substances with water.

By using the method of solution according to the invention, instead of the melting process described in German Offenlegungsschrift No. 2,355,743, the non-fusible solubilizing substance polyvinylpyrrolidone can be processed in molecular dispersion together with gliquidone or the anti-diabetic benzoic acid.

The solution to the problem described above is surprising for the following reasons:

The methods of incorporation of substances which are difficultly soluble in the digestive fluids, described in the literature and listed hereinafter, do not result in a significant increase in the dissolution rate of the active substance when applied to the production of compositions containing the above-mentioned active substances, nor can they improve the dissolution rate found for the commercially available preparations which contain oral anti-diabetics.

Some relevant testing is described hereinafter. The dissolution rates were determined, if not otherwise stated, after 5 and 30 minutes by the USP XX Paddle Method in 900 ml of McIlvaine Buffer, at pH 7.0, at 37° C. and at 100 rpm. For each measurement, a quantity of preparation corresponding to 40.0 mg of active substance was used, and each measurement was repeated twice. The average was calculated from the results obtained.

To determine the dissolution rate with an increase in the surface area of gliquidone, 30 parts by weight of the active substance were dissolved in 150 parts by weight of methylene chloride, and the solution was applied to 210 parts by weight of a tablet carrier. After drying, the treated tablet carrier was compressed to form tablets, and the dissolution rate of the gliquidone from these tablets was determined, 5% of the active substance dissolved after 5 minutes and 7% dissolved after 30 minutes. In the case of micronized gliquidone with no excipients, 0° dissolved after 5 and 30 minutes. When the micronized gliquidone was compressed to form tablets (see the comparison form in Example 1), 5.8% of active substance dissolved after 5 minutes and 7.2% after 30 minutes.

No better dissolution rate was obtained by forming gliquidone salts. Five parts by weight of gliquidone were dissolved in an aqueous solution of 1.9 parts by weight of ethylenediamine $\times H_2O$, while heating and stirring, the solution was dried in vacuo in a rotary evaporator, and the resulting solid product was passed through a 1.0 mm mesh screen. This product also yielded only 4% of dissolved active substance after 5 minutes and 30 minutes.

Not even the use of a gliquidone-containing dispersion produced any better dissolution rates. Analogous to the method described in German Offenlegungsschrift No. 2,355,743, 1.47 parts by weight of gliquidone were dissolved in a melt consisting of 79.1 parts by weight of polyglycol 4000 and 5.0 parts by weight of polyoxyethylene-40-stearate, and then 14.43 parts by weight of potassium bicarbonate were dispersed therein. The solidified melt was rubbed through a screen with a mesh size of 1.0 mm. The measurement of the dissolution rate gave a result of 10% of active substance after 5 minutes and 7% after 30 minutes.

A further series of tests was carried out to check whether the use of gliquidone salts in the process described in German Offenlegungsschrift No. 2,355,743 leads to better dissolution rates. Again, a melt consisting of 79.1 parts by weight of polyethylene glycol 4000 and 5.0 parts by weight of polyoxyethylene-40-stearate was used, in which a saturated solution of the gliquidone salt in question was prepared. Then, 14.43 parts by weight of potassium bicarbonate was dispersed in this solution. The solidified melt was passed through a screen with a mesh size of 1.0 mm.

TABLE 1

| Gliquidone Salt containing | Maximum Active Substance (calculated as base) Soluble in Melt Consisting of PEG 4000 and Polyoxyethylene-40-stearate (%) | Quantity of Solid Solution Required for 30 mg Gliquidone for Each Dose (gm) |
|---|---|---|
| Ethylenediamine | 0.65 | 4.6 |
| NH$_4$OH | 2.40 | 1.25 |
| N—glucamine | 0.54 | 5.54 |
| Piperidine | 2.15 | 1.395 |
| NaOH | 1.99 | 1.51 |

(PEG 4000 = polyethylene glycol 4000)

It is easy to see from these results that the quantity of melt required for 30 mg of gliquidone cannot be contained in a disintegrating table which can be swallowed. Thus, the process according to German Offenlegungsschrift No. 2,355,743 is unsuitable for gliquidone salts and also for the salts of the other active substances mentioned hereinbefore.

As can be seen from the tests described above, it is not possible to achieve rapid and total dissolution of the active substances, demonstrated on gliquidone, using the known methods which are described as suitable for such purposes.

When pharmaceutical compositions are developed, optimization is carried out be using in vitro methods. The release and dissolution cf the active substance are determined by means of dissolution tests. To create conditions comparable to those obtained in vivo, these tests are normally carried out in an acid medium at pH 1.2. If this pH is used with the compositions according to the invention containing gliquidone, no measurable release rates are obtained. In vitro dissolution tests must in this case therefore be carried out at pH 7 or higher. This is due to the fact that the solubility of the active substance is no longer sufficient at pH levels below 7. It would therefore be expected that there would be only a slight release of active substance in vivo in the acid range of the intestinal tract. The rapid and total absorption of the active substance, even in the upper region of the intestinal tract, is therefore surprising to anyone skilled in the art. It is also surprising that in spite of the difference between the in vivo situation and the measurement of the dissolution rate in vitro, there is considerable agreement between in vitro and in vivo. This is shown by a comparison of the dissolution rates in Example 2 in Table 2 with the curve in FIG. 1, on the one hand, and the curve for the composition according to Example 2 with the curves 'or the preparations of Examples 6 and 8, which are not according to the invention. For other active substances suitable pH-values derived from in-vivo results are to be chosen.

If the hypoglycemically active substances mentioned above are formulated by the processes described above, pharmaceutical compositions are obtained wherein the action of the active substance is matched to the physiological requirement of the patient for this medicament. These special pharmaceutical products ensure rapid and complete absorption of the active substance. Rapid absorption shortens the time which must elapse between taking of the medicament and taking of a meal to synchronize the hypoglycemic activity of the sulfonyl urea or benzoic acid with the increase in blood sugar caused by food intake. Rapid and total absorption reduces intra- and interindividual fluctuations in the blood glucose level, minimizes the dependence of absorption on the state of the gastrointestinal tract or on the nature or quantity of food taken, and thus ensures the correct metabolic pattern and consequently a correct insulin release. The disadvantages described above relating to the forms known at present are avoided by using the process according to the invention.

Trials on humans (see FIG. 1) demonstrated the rapid start of action of the preparation according to the invention (Example 2) and the slight activity of Examples 6 and 8, which are not according to the invention. It is also found that the values obtained in vitro and in vivo correspond well.

The findings mentioned above show that the medical objectives of (a) avoiding a non-physiological rise in blood sugar after intake of food, and (b) avoiding a massive drop in blood sugar some hours after food intake, are achieved with the compositions according to the invention.

The methods of measurement used were as follows:

Determining the Blood Glucose

The blood sugar was measured in whole venous blood. Fifty microliters of blood were freed from protein with 500 μl of 0.32M perchloric acid. After centrifuging, the glucose in the supernatant was measured by the hexokinase method, using an automatic substrate.

Human Testing

Blood samples were taken through long-term catheters with heparinized disposable syringes. After a preliminary period of 15 minutes in which the course of the blood sugar level and of the insulin level without any medicament was measured, the galenic preparation was administered in the form of a granulate or in tablet form in the appropriate dosage with 70 ml of water.

The essence of the invention will be investigated more closely hereinafter in a discussion of the results obtained in the tests described in the examples.

Table 2 shows the correlation between the quantity of polyvinylpyrrolidone and the dissolution rate.

Table 3 shows that the presence of an alkaline excipient is absolutely necessary, not only for dissolving gliquidone but also for obtaining rapid release of the active substance. To achieve an equally high dissolution rate solely by using the solubilizing carrier KOLLIDON 25® without using an alkaline excipient, the quantity of KOLLIDON 25 in this example would have to be increased by almost a power of 10. However, such a high proportion of polyvinylpyrrolidone is impossible for practical reasons—the preparations would no longer be manageable as oral preparations, and in any case, such forms would not be viable from the point of view of manufacture and cost.

The following examples are intended to illustrate the invention and should not be construed as limiting the invention thereto. In these examples, the following substances were employed:

AVICEL®, a microcrystalline cellulose available from FMC Export Corporation, Philadelphia, Pa.;

KOLLIDON 25, a poly-N-vinylpyrrolidone(-2), available from BASF, D-6700 Ludwigshafen (West Germany);

PLURONIC® F 68, a polyoxyethylene polyoxypropylene polymer, available from Wyandotte Chemicals Corp., Wyandotte, Mich.;

EXPLOTAB®, a sodium carboxymethyl starch, available from Eastman Kodak Co., Rochester, N.Y.;

PEG 4000 = polyethylene glycol 4000; and

AMBERLITE® IRP 88, a potassium salt of polymers of methacrylic acid and divinylbenzene (methacrylic acid polymer with vinylbenzene, potassium salt), available from Rohm and Haas Deutschland GmbH, Philadelphia, Pa.

EXAMPLES

Examples 1 to 3

Table 2 contains Examples 1 to 3 with their dissolution rates. The compositions of Examples 1 to 3 each contained 5 mg of gliquidone and 1.9 mg of ethylenediamine $\times H_2O$.

TABLE 2

| Example No. | KOLLIDON 25 (mg) | Dissolution Rate in percent of Active Substance Which Went into Solution | |
|---|---|---|---|
| | | After 5 mins. | After 30 mins. |
| 1 | 10 | 91 | 93 |
| 2 | 30 | 95 | 97 |
| 3 | 60 | 92 | 96 |

The compositions in these Examples were prepared as follows:

The basic excipient was dissolved in 100 parts by weight of water at 70° C. while stirring. The active substance was added, and the mixture was stirred until the active substance was completely dissolved. Polyvinylpyrrolidone was dissolved in this solution. The solution was evaporated to dryness in vacuo while stirring, and the residue was rubbed through a screen with a mesh size of 1 mm.

A comparison with a known gliquidone-containing preparation of the following composition:
Micronized gliquidone: 30 parts by weight
Corn starch: 75 parts by weight
Lactose: 132 parts by weight
Magnesium stearate: 3 parts by weight
showed the following dissolution rate:
5.8% of gliquidone after 5 minutes;
7.2% of gliquidone after 30 minutes.

Examples 4 and 5

The compositions shown in Table 3 below contained, in addition to 5 mg of gliquidone, increasing quantities of polyvinylpyrrolidone (KOLLIDON 25) but no basic excipient and no carrier. A useful dissolution rate was achieved only with upwards of 12 times the quantity of KOLLIDON 25.

The compositions in these Examples were produced by dissolving the active substance and solubilizing substance together in ethanol. The solution was then evaporated to dryness, and the residue was rubbed through a screen with a mesh size of 1 mm.

TABLE 3

| Example No. | KOLLIDON 25 (mg) | Dissolution Rate in percent of Active Substance Which Went into Solution | |
|---|---|---|---|
| | | After 5 mins. | After 30 mins. |
| 4 | 10 | 24 | 44 |
| 5 | 60 | 90 | 93 |

Examples 6 to 8

The composition in Example 7 was prepared as described in Example 1. The compositions of Examples 6 and 8 were produced in analogy to the method described in Examples 4 and 5.

Table 4 shows the compositions and the dissolution rates measured. As can be seen from Table 4, the presence of a basic excipient alone does not lead to a useful dissolution rate, nor does the sole presence of a solubilizing substance (without a basic excipient and a carrier) lead to a product with a useful dissolution rate. This shows that the combination of gliquidone with a basic excipient and solubilizing agent in the presence of a water-insoluble carrier yields the best results in terms of rapid and fullest possible dissolution of the active substance.

TABLE 4

| Example No. | Gliquidone (mg) | Basic Excipient | Solubilizing Agent | Dissolution Rate in Percent of Active Substance Which Went into Solution | |
|---|---|---|---|---|---|
| | | | | After 5 mins | After 30 mins |
| 6 | 5 | 1.9 mg of Ethylenediamine $\times H_2O$ | — | 4 | 4 |
| 7 | 25 | 6.5 mg of Ethylenediamine $\times H_2O$ | 30 mg of KOLLIDON 25 | 88 | 94 |
| 8 | 25 | — | 30 mg of KOLLIDON 25 | 12 | 24 |
| 9 | 30 | 36.0 mg of L-Lysine | 20 mg of KOLLIDON 25 + 24 mg of PLURONIC F 68 | 91 | — |

Example 9

| Component | Amount (mg) |
|---|---|
| Gliquidone | 30.0 |
| L-lysine | 36.0 |
| KOLLIDON 25 | 20.0 |
| PLURONIC F 68 | 24.0 |

Processing was carried out in analogy to Examples 1 to 3, but with the solution being evaporated in a spray dryer.
The following were added per tablet.

| | |
|---|---|
| | 105.0 mg AVICEL |
| | 105.0 mg EXPLOTAB |
| TOTAL: | 320.0 mg |

From this mixture round biconvex tablets weighing 320 mg and measuring 10 mm in diameter were compressed and coated with hydroxypropyl methylcellulose to mask the flavor. Dissolution rate: 91% of gliquidone after 5 minutes.

Example 10

Film-coated tablets containing 4-[(1-(2-piperidono-phenyl)-1-butyl)-amino-carbonylmethyl]-benzoic acid

| Component | Amount (mg) |
|---|---|
| 4-[(1-(2-Piperidino-phenyl)-1-butyl)-aminocarbonylmethyl]-benzoic acid | 30 |
| AMBERLITE IRP 88 | 134 |
| AVICEL | 134 |
| Magnesium stearate | 2 |
| TOTAL: | 300 |

The tablet components were mixed together, compressed to form round biconvex tablets weighing 300 mg and measuring 10 mm in diameter, and then coated with hydroxypropyl methylcellulose to mask the flavor.
Dissolution rate: 25.6% of active substance after 5 minutes; 36.3% of active substance after 30 minutes.

(b) A granulate of active substance had the following composition:

| Component | Amount (g) |
|---|---|
| Active substance of Example 10(a) | 30 |
| L-lysine | 36 |
| KOLLIDON 25 | 30 |
| PLURONIC F 68 | 24 |

Processing was carried out in analogy to Examples 1 to 3. The following were added to this granulate:

| | |
|---|---|
| | 90 mg AVICEL |
| | 90 mg AMBERLITE IRP 88 |
| TOTAL: | 300 mg |

Round biconvex tablets weighing 300 mg and measuring 10 mm in diameter were compressed from this mixture and coated with hydroxypropyl methylcellulose to mask the flavor.
Dissolution rate: 48.7% of active substance after 5 minutes; 81.3% of active substance after 30 minutes.

Example 11

Film-coated tablets containing 4-[N-(α-phenyl-2-piperidinobenzyl)-aminocarbonylmethyl]-benzoic acid
(a) Each tablet had the following composition:

| Component | Amount (mg) |
|---|---|
| Active substance | 30 |
| AMBERLITE IRP 88 | 134 |
| AVICEL | 134 |
| Magnesium stearate | 2 |
| TOTAL: | 300 |

The tablet ingredients were mixed together, compressed to form round biconvex tablets weighing 300 mg and measuring 10 mm in diameter, and coated with hydroxypropyl methylcellulose to mask the flavor.
Dissolution rate: 15.8% of active substance after 5 minutes; 20.9% of active substance after 30 minutes.

(b) A granulate of active substance had the following composition:

| Component | Amount (mg) |
|---|---|
| Active substance of Example 11(a) | 30 |
| L-lysine | 30 |
| KOLLIDON 25 | 30 |
| PLURONIC F 68 | 24 |

Processing was carried out in analogy to Examples 1 to 3. The following were added to this granulate:

| | |
|---|---|
| | 93 mg AVICEL |
| | 93 mg AMBERLITE IRP 88 |
| TOTAL: | 300 mg |

Round biconvex tablets weighing 300 mg and measuring 10 mm in diameter were compressed from this mixture and coated with hydroxypropyl methylcellulose to mask the flavor.
Dissolution rate: 58.4% of active substance after 5 minutes; 93.4% of active substance after 30 minutes.

Example 12

Film-coated tablets containing 4-[2-(5-chloro-2-octamethyleneimino-benzoyl-amino)-ethyl]-benzoic acid
(a) Each tablet had the following composition:

| Component | Amount (mg) |
|---|---|
| Active substance | 30 |
| AMBERLITE IRP 88 | 134 |
| AVICEL | 134 |
| Magnesium stearate | 2 |
| TOTAL: | 300 |

The tablet ingredients were mixed together, compressed to form round biconvex tablets weighing 300 mg and measuring 10 mm in diameter, and then coated with hydroxypropyl methylcellulose to mask the flavor.
Dissolution rate: 18.4% of active substance after 5 minutes; 27.2% of active substance after 30 minutes.

(b) A granulate of active substance had the following composition:

| Component | Amount (mg) |
|---|---|
| Active substance of Example 12(a) | 30 |
| L-lysine | 36 |
| KOLLIDON 25 | 30 |
| PLURONIC F 68 | 24 |

Processing was carried out in analogy to Examples 1 to 3.

The following were added to the granulate:

| | |
|---|---|
| | 900 mg AVICEL |
| | 900 mg AMBERLITE IRP 88 |
| TOTAL: | 3000 mg |

Round biconvex tablets weighting 300 mg and measuring 10 mm in diameter were compressed from this mixture and coated with hydroxypropyl methylcellulose to mask the flavor.

Dissolution rate: 96.2% of active substance after 5 minutes; 99.9% of active substance after 30 minutes.

EXAMPLE 13

Tablets containing 2-Ethoxy-4-{2-oxo-2-[(α-isobutyl-2-piperidino-benzyl)-amino]ethyl? -benzoic acid of the formula

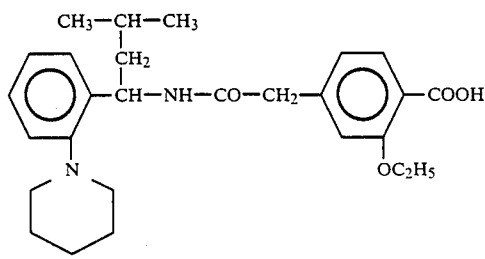

This active substance is of amphoteric character. When the following reference Example 13a (without the addition of an acid or a base) is compared with Example 13b (with base) and 13c (with acid) with respect to the dissolution rate, it becomes apparent that, especially in the pH-range between 3 and 6 (the range of poorest solubility of the active substance), the addition of a base or an acid together with the solubilizing agent results in a very good dissolution rate.

(a) Each table had the following composition:

| Component | Amount (mg) |
|---|---|
| Active substance | 10.0 |
| Lactose | 215.0 |
| AVICEL | 44.0 |
| AMBERLITE IRP 88 | 30.0 |
| Magnesium stearate | 1.0 |
| TOTAL: | 3000 |

Preparation

The active substance and the excipients were uniformly admixed with each other, and the mixture was compressed into tablets with a diameter of 10 mm and 300 mg weight.

Determination of the dissolution rate

It was carried out in 900 ml of buffer of pH 1.2, 2.0, 3.0, 4.0, 6.0 or 7.0 at 37° C. and 100 rpm according to USP XXI/paddle method.

Sample taking

After 5, 10, 30 and 60 minutes.

The results are shown in FIGS. 2 through 5 of the attached drawings.

(b) Each tablet had the following composition:

| Component | Amount (mg) |
|---|---|
| (01) Active substance | 10.0 |
| (02) PLURONIC F 68 | 5.0 |
| (03) KOLLIDON 25 | 5.0 |
| (04) Lysine × H$_2$O | 5.0 |
| (05) Lactose | 160.0 |
| (06) AVICEL pH 101 | 44.0 |
| (07) AMBERLITE IRP 88 | 30.0 |
| (08) Magnesium stearate | 1.0 |
| TOTAL: | 260.0 |

The mol ratio of active substance to lysine ×H$_2$O is 1:1.38.

Preparation

Ingredients (02), (03) and (04) were dissolved in aqueous ammonia, ingredient (01) was added thereto and dissolved a 85° C. The solution was processed into a spray granulate by means of a spray drier. The spray granulate was admixed with the remaining tablet excipients (05), (06), (07) and (08), and the resulting mixture was compressed into tablets having a diameter of 10 mm and a weight of 260.0 mg.

Determination of the dissolution rate and sample taking: see Example 13a.

c) Each tablet had the following composition:

| Component | Amount (mg) |
|---|---|
| (01) Active substance | 10.0 |
| (02) PLURONIC F 68 | 20.0 |
| (03) Tartaric acid | 100.0 |
| (04) KOLLIDON 25 | 20.0 |
| (05) AVICEL pH 101 | 40.0 |
| (06) Lactose | 117.0 |
| (07) AMBERLITE IRP 88 | 40.0 |
| (08) AEROSIL 200 | 2.0 |
| (09) Magnesium stearate | 1.0 |
| TOTAL: | 350.0 |

Preparation

Ingredients (02), (03) and (04) were dissolved in water, and thereafter ingredient (01) was dissolved in this solution at 60° C. The resulting solution was processed into a spray granulate in a spray drier, and subsequently the remaining excipients (05), (06), (07), (08) and (09) were admixed with the granulate. This mixture was compressed into tablets having a weight of 350.0 mg and a diameter of 10 mm.

Determination of the dissolution rate

It was carried out in 900 ml of buffer of pH 5.0 (the active substance has the poorest solubility at this pH) at 37° C. and 100 rpm in accordance with USP XXI/paddle-method.

Result

After 5 minutes 99 percent of the active substance went into solution.

Example 14

Tablets containing 4-[N-(2-Piperidino-α-propylbenzyl)carbamoylmethyl]benzoic acid of the formula

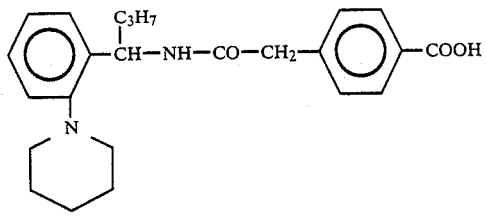

a) Tablets without addition of acid.
Each tablet had the following composition:

| Component | Amount (mg) |
| --- | --- |
| (01) Active substance | 20.0 |
| (02) KOLLIDON 25 | 6.6 |
| (03) PLURONIC F 68 | 13.4 |
| (04) Mannitol | 27.0 |
| (05) Calcium hydrogen phosphate × 2H$_2$O | 240.0 |
| (06) AMBERLITE IRP 88 | 30.0 |
| (07) AVICEL pH 101 | 41.5 |
| (08) Magnesium stearate | 1.5 |
| TOTAL: | 380.0 |

Preparation

Ingredients (02), (03) and (04) were dissolved in dilute aqueous ammonia. Ingredient (01) was in turn dissolved in this solution at 75° C. The resulting solution was processed into a spray granulate in a spray dryer. The remaining excipients (05), (06), (07) and (08) were admixed with the granulate, and the mixture was compressed into tablets having a weight of 380.0 mg and a diameter of 10 mm.

Determination of the dissolution rate

It was carried out in 900 ml buffer of pH 4, pH 5 and pH 6 at 37° C. and 100 rpm according to USP XXI/paddle-method.

Results

Percentage release or dissolution of the active ingredient:

| after minutes | at pH 4 | at pH 5 | at pH 6 |
| --- | --- | --- | --- |
| 5 | 20 | 18 | 27 |
| 10 | 26 | 24 | 38 |
| 30 | 38 | 34 | 55 |

(b) Tables with addition of acid
Each tablet had the following composition:

| Component | Amount (mg) |
| --- | --- |
| (01) Active substance | 10.0 |
| (02) Tartaric acid | 100.0 |
| (03) PLURONIC F 68 | 20.0 |
| (04) KOLLIDON 25 | 20.0 |
| (05) AVICEL pH 101 | 40.0 |
| (06) Lactose | 117.0 |
| (07) AMBERLITE IRP 88 | 40.0 |
| (08) AEROSIL 200 | 2.0 |
| (09) Magnesium stearate | 1.0 |
| TOTAL: | 350.0 |

Preparation

Ingredients (02), (03) and (04) were dissolved in water, and ingredient (01) was dissolved in this solution at 96° C. The resulting solution was processed into a spray granulate in a spray drier, and the remaining excipients were admixed with the granulate. The resulting mixture was compressed into tablets having a weight of 350.0 mg and a diameter of 10 mm.

Determination of the dissolution rate

It was carried out according to USP XXI/paddle-method in 900 ml buffer of pH 5.0 (in this pH range the active substance exhibits the poorest solubility) at 37° C. and 100 rpm.

Results

After 5 minutes 85 percent by weight of the active substance was dissolved,
after 10 minutes 92 percent by weight of the active substance was dissolved and
after 30 minutes 97 percent by weight of the active substance was dissolved.

The anti-diabetic substances used according to the invention are administered orally, optionally in combination with other active ingredients, in conventional manner. The daily dose for adults is from about 5 to 150 mg (from about 0.07 to 2 mg/kg body weight), preferably from about 10 to 120 mg (from about 0.18 to 1.6 mg/kg body weight), generally administered in the form of several, preferably from 2 to 4, individual doses to achieve the desired results. Depending upon the type and body weight of the patient to be treated, on the type and severity of the disease, on the type of preparation and on the route of administration as well as on the period or interval over which the administration takes place, it may, however, be necessary to deviate from the above dosages. Thus it may be sufficient in some cases to administer more or less than the above-mentioned amounts of active ingredient. The optimum dosage and route of administration of the active ingredients which are necessary in each case can easily be determined by one skilled in the art.

The compositions prepared according to the instant invention can be further processed to produce pharmaceutical compositions useful for administration according to the invention. For example, the compositions can be admixed with conventional pharmaceutical excipients to form tablets, coated tablets, capsules, solutions, and the like. Such conventional excipients include, for example, microcrystalline cellulose, potassium salts of polymers of methacrylic acid and divinylbenzene, magnesium stearate, lactose, corn starch, polyvinylpyrrolidone, gelatin and the like.

The following is an example of such pharmaceutical compositions:

Example 15

Capsules

A quantity of granulate from Example 1 corresponding to 10 mg of gliquidone is mixed with a corresponding quantity of corn starch and magnesium stearate. The resulting mixture is then filled into size 4 hard gelatin capsules.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. The method of preparing an oral antidiabetic pharmaceutical composition containing an antidiabetic benzoic acid as the active ingredient, which comprises dissolving
    (a) an acidic antidiabetic benzoic acid with a basic excipient, or
    (b) an amphoteric antidiabetic benzoic acid with a basic or acidic excipient, or
    (c) a basic antidiabetic benzoic acid with an acidic excipient
and polyvinylpyrrolidone in an inert polar solvent, where the molar ratio of benzoic acid to basic or acidic excipient is less than 1:1 and the ratio of benzoic acid to polyvinylpyrrolidone is from about 1:0.5 to 1:10 parts by weight, and evaporating the resulting solution to dryness.

2. The method of claim 1, where said benzoic acid is -Ethoxy-4-{2-oxo-2-[(α-isobutyl-2-piperidino-benzyl)-amino]ethyl}-benzoic acid.

3. The method of claim 1, where said benzoic acid is -[N-(α-phenyl-2-piperidino-benzyl)-aminocarbonylmethyl]benzoic acid.

4. The method of claim 1, where said benzoic acid is 4-[N-(2-Piperidino-α-propylbenzyl)-carbamoylmethyl]-benzoic acid.

5. The method of claim 1, where said basic excipient is ethylenediamine or L-lysine, and said acidic excepient is sulfuric acid, phosphoric acid or tartaric acid.

6. The method of claim 1, which comprises dissolving 2-Ethoxy-4-{2-oxo-2-[(α-isobutyl-2-piperidino-benzyl)-amino]ethyl}-benzoic acid with a basic or acidic excipient in an inert polar solvent, where the molar ratio of said benzoic acid to basic or acidic excipient is less than 1:1, dissolving polyvinylpyrrolidone in the resulting solution, the ratio of said benzoic acid to polyvinylpyrrolidone being about 0.5 to 1:10 parts by weight, and evaporating the solution thus obtained to dryness.

7. The method of claim 1, where the molar ratio of said benzoic acid to basic or acidic excipient is about 1:1.1 to 110.

8. The method of claim 1, where said conventional pharmaceutical excipient includes an additional solubilizing agent.

9. An oral antidiabetic pharmaceutical composition consisting essentially of a conventional pharmaceutical excipient and the evaporation residue of a solution of an effective antidiabetic amount of an acidic, amphoteric or basic antidiabetic benzoic acid, a basic or acidic excipient and polyvinylpyrrolidone in an inert polar solvent, where the molar ratio of benzoic acid to basic or acidic excipient is less than 1:1 and the ratio of benzoic acid to polyvinylpyrrolidone is about 1:0.5 to 1:10 by weight.

10. A composition of claim 9, where said benzoic acid is 2-Ethoxy-4-{2-oxo-2-[(α-isobutyl-2-piperidino-benzyl)-amino]-ethyl}-benzoic acid.

11. A composition of claim 9, where said benzoic acid is 4-[N-(α-phenyl-2-piperidino-benzyl)-aminocarbonylmethyl]benzoic acid.

12. A composition of claim 9, where said benzoic acid is 4-[N-(2-Piperidino-α-propylbenzyl)-carbamoylmethyl]benzoic acid.

13. A composition of claim 9, where said basic excipient is ethylenediamine or L-lysine, and said acidic excepient is sulfuric acid, phosphoric acid or tartaric acid.

14. A composition of claim 9, where the molar ratio of said benzoic acid to basic or acidic excipient is from 1:1.1 to 1:10.

15. A composition of claim 9, wherein said conventional pharmaceutical excipient includes additional solubilizing agent.

16. The method of claim 1, wherein the evaporation residue is combined with a conventional pharmaceutical excipient to produce the desired oral antidiabetic pharmaceutical composition.

17. The method of claim 6 wherein the evaporation residue is combined with a conventional pharmaceutical excipient to produce the desired oral antidiabetic pharmaceutical composition.

* * * * *

UNITED STATES PATENT AND TRADEMARK OFFICE
CERTIFICATE OF CORRECTION

PATENT NO. : 4,863,724

DATED : September 5, 1989

INVENTOR(S) : Gottfried Schepky et al

It is certified that error appears in the above-identified patent and that said Letters Patent is hereby corrected as shown below:

Column 5, line 30, In Table 1, "N-glucamine" should read --N-Methylglucamine--.

Column 5, line 48, "cf" should read --of--.

Column 6, line 2, " 'or" should read --for--.

Column 11, line 14, "900" should read --90.0--.

Column 11, line 15, "900" should read --90.0--.

Column 11, line 16, "3000" should read --300.0--.

Column 11, line 27, "amino]ethyl?" should read --amino]ethyl}--.

Column 11, line 61, "3000" should read --300.0--.

Column 15, line 34, "-Ethoxy" should read --2-Ethoxy--.

Column 15, line 37, "-[N($\alpha$-phenyl" should read --4-[N-($\alpha$-phenyl--.

UNITED STATES PATENT AND TRADEMARK OFFICE
CERTIFICATE OF CORRECTION

PATENT NO. : 4,863,724

DATED : September 5, 1989

INVENTOR(S) : Gottfried Schepky et al

It is certified that error appears in the above-identified patent and that said Letters Patent is hereby corrected as shown below:

Column 16, line 4, "0.5" should read --1:0.5--.

Column 16, line 8, "110" should read --1:10--.

Signed and Sealed this

Twenty-fifth Day of September, 1990

Attest:

HARRY F. MANBECK, JR.

*Attesting Officer*     *Commissioner of Patents and Trademarks*